United States Patent [19]
Rauch et al.

[11] 3,983,010
[45] Sept. 28, 1976

[54] RECOVERY OF THE FORMIC ACID/WATER AZEOTROPE BY DISTILLATION

[75] Inventors: Konrad Rauch, Limburgerhof; Hans Kiefer, Wachenheim; Dieter Hesse, Frankenthal; Max Strohmeyer, Limburgerhof; Heinz Hohenschutz, Mannheim, all of Germany

[73] Assignee: BASF Aktiengesellschaft, Ludwigshafen (Rhine), Germany

[22] Filed: Feb. 6, 1975

[21] Appl. No.: 547,642

[30] Foreign Application Priority Data
Feb. 15, 1974 Germany............................ 2407157

[52] U.S. Cl................................... 203/15; 260/499; 260/542; 203/99
[51] Int. Cl.²........................................... C07C 51/44
[58] Field of Search .............. 260/499, 542; 203/12, 203/14, 15, 16

[56] References Cited
UNITED STATES PATENTS

| | | |
|---|---|---|
| 1,826,302 | 10/1931 | Clarke et al. ......................... 203/15 |
| 1,896,100 | 2/1933 | Ricard et al. ......................... 203/15 |
| 3,404,175 | 10/1968 | Mercier ................................ 203/14 |
| 3,681,204 | 8/1972 | Mercier ................................ 203/14 |
| 3,692,636 | 9/1972 | Huguet ............................... 260/499 |
| 3,718,545 | 2/1973 | Horlenko ............................ 203/15 |
| 3,769,177 | 10/1973 | Eubanks et al. ...................... 203/15 |
| 3,791,935 | 2/1974 | Eubanks et al. ...................... 203/15 |

Primary Examiner—Frank W. Lutter
Assistant Examiner—Frank Sever
Attorney, Agent, or Firm—Johnston, Keil, Thompson & Shurtleff

[57] ABSTRACT

Formic acid is isolated from mixtures containing formic acid, methyl formate, methanol and water by fractional distillation, the mixture being fed into the upper half of the distillation column and 5 to 15 theoretical plates being maintained above the feed point and 10 to 25 theoretical plates below the feed point. The formic acid is withdrawn at the bottom end of the column as an azeotrope with water, the azeotrope being in the liquid state or preferably in the vapor state.

3 Claims, 1 Drawing Figure

LEGEND
MF METHYL FORMATE
M METHANOL
W WATER
FA FORMIC ACID

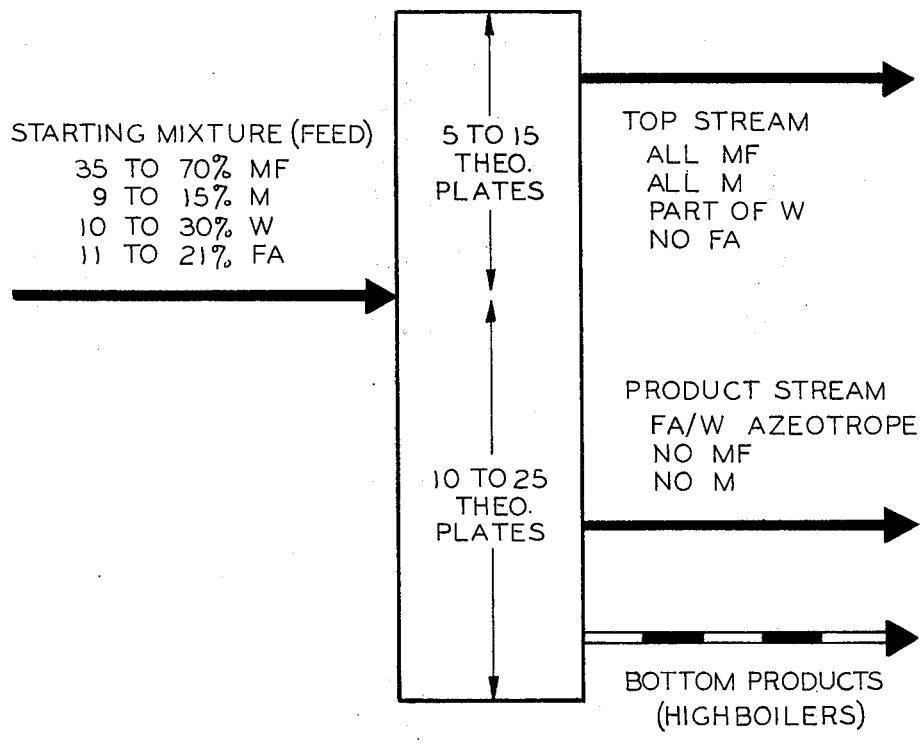

RECOVERY OF THE FORMIC ACID/WATER AZEOTROPE BY DISTILLATION

This application discloses and claims subject matter described in German Patent Application No. P 24 07 157.6, filed Feb. 15, 1974, which is incorporated herein by reference.

The present invention relates to a process for isolating formic acid from mixtures containing methyl formate, water, methanol and formic acid by fractional distillation in a column.

Published German Patent Application No. C 9713 IVb/12 o discloses a process in which reaction mixtures obtained by hydrolysis of carboxylic acid esters with water and containing, in accordance with the ester equilibrium, carboxylic acid ester, alcohol, water and carboxylic acid, are worked up by distillation in a column, the carboxylic acid being isolated. However, the process suffers from the disadvantage that the carboxylic acid is obtained as an aqueous solution which is very dilute, eg. of from 20 to 40 per cent strength by weight. Removing such large amounts of water so as to isolate more concentrated carboxylic acids requires considerable technical effort. In addition, the above process is not applicable to mixtures obtained by hydrolysis of methyl formate since, as disclosed by British Patent No. 1,196,085, page 1, lines 29 et seq., formic acid itself serves as an esterification catalyst. The consequence of this is that even in the absence of conventional esterification catalysts, such as strong mineral acids, a not inconsiderable degree of re-esterification occurs during distillation and substantially reduces the yield of free formic acid.

It is an object of the present invention to provide a method of carrying out the distillation of hydrolysis mixtures containing methyl formate, methanol, water and formic acid in such a way that the formic acid is obtained as an azeotrope with water and at the same time the re-esterification of formic acid with methanol is repressed as much as possible.

We have found that formic acid can be isolated more advantageously than hitherto from mixtures containing methyl formate, water, methanol and formic acid by fractional distillation in a column, if (1) the starting mixture is fed into the upper half of the distillation column, (2) a zone of 5 to 15 theoretical plates, in which the formic acid concentration decreases, is maintained above the feed point of the starting mixture, (3) a mixture of water, methanol and methyl formate is taken overhead, (4) a zone of 10 to 25 theoretical plates, in which the formic acid concentration increases until the composition corresponds to the formic acid/water azeotrope, is maintained below the feed point and (5) the formic acid/water azeotrope is withdrawn near the bottom of the column.

The number of actual plates corresponding to the number of theoretical plates depends in known manner on the design of the column.

The advantage of the new process is that the re-esterification of formic acid in the hydrolysis mixture used as the starting material is restricted to a minimum. Another advantage is that the formic acid is obtained as an azeotrope of constant concentration.

The starting mixture used contains methyl formate, water, methanol and formic acid. Such mixtures as a rule contain from 35 to 70 per cent by weight of methyl formate, from 9 to 15 per cent by weight of methanol, from 10 to 30 per cent by weight of water and from 11 to 21 per cent by weight of formic acid. The preferred starting mixtures when operating the process industrially have a composition corresponding, or substantially corresponding, to the ester equilibrium. Such mixtures contain about 54 per cent by weight of methyl formate, 16 per cent by weight of water, 12 per cent by weight of methanol and 17 per cent by weight of formic acid and are obtained by hydrolysis of methyl formate with water in the presence of acid catalysts, such as sulphuric acid.

The distillation is carried out in a single column. Examples of suitable columns are bubble-cap plate columns, sieve plate columns, packed columns, valve plate columns or dual flow columns.

The columns used have from 15 to 40, in particular from 20 to 30, theoretical plates.

The starting mixture is introduced into the upper half of the column, preferably at from 7 to 10 theoretical plates below the top of the column. A zone of from 5 to 15 theoretical plates, advantageously from 5 to 12 theoretical plates and in particular from 7 to 10 theoretical plates, in which the formic acid content decreases virtually to zero, is maintained above the feed point. A mixture of water, methanol and methyl formate is withdrawn overhead. The mixture as a rule contains about 15 per cent by weight of methanol, about 70 per cent by weight of methyl formate and about 15 per cent by weight of water. Below the feed point, a zone of from 10 to 25 theoretical plates, especially of from 13 to 20 theoretical plates, is maintained, in which the content of formic acid increases until the mixture reaches the composition of the formic acid/water azeotrope (75 per cent by weight of formic acid and 25 per cent by weight of water). This azeotrope, preferably in the vapor state, is withdrawn from the column at the point at which the formic acid/water azeotrope is present, which is also the end of the zone below the feed point.

It is advantageous not to withdraw the formic acid/water azeotrope from the bottom of the column but a few plates, eg. from 1 to 3 theoretical plates, above the bottom, preferably as a side-stream in the vapor state, whilst any high-boiling constituents which may be present are discharged in a concentrated form, from the bottom.

It is advantageous to maintain a reflux ratio of from 0.5 to 2 : 1 during the distillation, which is generally carried out under atmospheric pressure but can also be carried out under slightly elevated pressure (eg. at up to 1 atmosphere gauge). The top of the column is generally maintained at from 80° to 90°C and the bottom at from 105° to 115°C.

The aforedescribed process is illustrated in the accompanying drawing, which constitutes a diagrammatic illustration of the distillation column, the composition of the starting mixture or feed and the compositions of the product stream, the top or overhead stream, and the bottom products.

Formic acid obtained by the process of the invention can be used directly, without additional purification, as a preservative for green forage or be used to produce anhydrous formic acid by conventional methods, eg. by extraction.

The Examples which follow illustrate the process of the invention.

EXAMPLE 1

A bubble-cap plate column with 28 plates (corresponding to 20 theoretical plates) operated at atmospheric pressure and having a plate efficiency of 0.71 is fed, at the level of the 19th plate (13th theoretical plate) with 1,000 parts/hour of a mixture consisting of 54.6% of methyl formate, 11.9% of methanol, 16.3% of water and 17.2% of formic acid. 742 parts/hour of a distillate containing 71.0% of methyl formate, 15.1% of methanol and 13.9% of water are withdrawn at the top of the column, which is at 80°C. An equal amount per hour is returned to the top of the column as reflux (giving a reflux ratio of 1 : 1). The formic acid is withdrawn as vapor from the column between the 2nd and 3rd plates. Condensation of the vapor gives 225 parts of a 75.1% strength formic acid. The proportion of re-esterification is only 1.7%, ie. the yield of formic acid is 98.3%, based on conversion. The formic acid contained in the side-stream withdrawn is free from any organic impurities.

If the feed is free from impurities, no product is withdrawn from the bottom of the column (which is at 112°C). If high-boiling impurities are present, they can be discharged in a concentrated form from the bottom of the column, in the conventional way.

COMPARATIVE EXAMPLE

The procedure described in Example 1 is followed, but the feed point is at the 11th plate (8th theoretical plate). Under otherwise completely analogous experimental conditions, the overhead consists of 801 parts/hour containing 59.6% of methyl formate, 11.2% of methanol and 16.2% of water. Only 175 parts/hour of a 74.5% strength formic acid are obtained between the 2nd and 3rd plates. Accordingly, the proportion of re-esterification is 22.4%, ie. only 77.5% of the formic acid present in the column feed are obtained as utilizable formic acid.

EXAMPLE 2

4,000 parts/hour of a mixture consisting of 42.4% of methyl formate, 18.4% of methanol, 21.9% of water and 17.5% of formic acid are fed onto the 19th and 20th plates (13th theoretical plate) of a sieve plate column having 33 plates with a plate efficiency of 0.65, ie. having 21.5 theoretical plates. Using a reflux ratio of 1 : 1, 3,009 parts/hour, containing 55.5% of methyl formate, 21.3% of water and 23.2% of methanol are withdrawn from the top of the column, which is at 85°C. The formic acid is withdrawn as vapor, between the 3rd and 4th plates, in an amount of 901 parts/hour and a concentration of 75.0%. The proportion of re-esterification is only 3.4%. The formic acid obtained is free from impurities and can be used directly for numerous purposes, including its use as a preservative.

We claim:

1. A process for the recovery of aqeuous solutions of about 75 weight percent formic acid and about 25 weight percent water from a starting mixture containing 35 to 70 weight percent of methyl formate, 9 to 15 weight percent of methanol, 10 to 30 weight percent of water and 11 to 21 weight percent of formic acid by fractional distillation in a column maintained at a temperature range of from 80° to 90°C at the top of the column to 105° to 115°C at the bottom, which comprises feeding said starting mixture into the upper half of the column, maintaining a zone of 5 to 15 theoretical plates, in which the formic acid concentration decreases relative to its concentration in said starting mixture, above the feed point of the starting mixture, withdrawing a mixture of water, methanol and methyl formate at the top of the column, maintaining below said feed point a zone of 10 to 25 theoretical plates, in which the formic acid concentration increases relative to its concentration in said starting mixture until the formic acid/water mixture reaches the composition of its azeotrope, which consists of about 75 weight percent formic acid and about 25 weight percent water, and withdrawing the formic acid/water azeotrope from the bottom portion of the column.

2. A process as claimed in claim 1, wherein the formic acid/water azeotrope is withdrawn as vapor a few plates above the bottom of the column.

3. A process as claimed in claim 1, wherein the starting mixture corresponds, or substantially corresponds, to the esterification equilibrium.

* * * * *